United States Patent
Shimizu et al.

(10) Patent No.: US 9,687,291 B2
(45) Date of Patent: Jun. 27, 2017

(54) TREATMENT SYSTEM

(71) Applicant: OLYMPUS CORPORATION, Tokyo (JP)

(72) Inventors: Ko Shimizu, Musashino (JP);
Yoshitaka Honda, Hachioji (JP);
Sumihito Konishi, Akishima (JP);
Tsuyoshi Hayashida, Hachioji (JP);
Akinori Kabaya, Berlin (DE)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/953,235

(22) Filed: Nov. 27, 2015

(65) Prior Publication Data

US 2016/0074093 A1    Mar. 17, 2016

Related U.S. Application Data

(63) Continuation of application No. PCT/JP2014/079252, filed on Nov. 4, 2014.

(30) Foreign Application Priority Data

Nov. 11, 2013  (JP) .................................. 2013-233252

(51) Int. Cl.
*A61B 18/12* (2006.01)
*A61B 18/16* (2006.01)
(Continued)

(52) U.S. Cl.
CPC ...... *A61B 18/1233* (2013.01); *A61B 18/1206* (2013.01); *A61B 18/14* (2013.01);
(Continued)

(58) Field of Classification Search
CPC .. A61B 2018/1273; A61B 2018/00636; A61B 18/1233; A61B 2018/165
(Continued)

(56) References Cited

U.S. PATENT DOCUMENTS

2003/0163124 A1    8/2003   Goble
2006/0200120 A1*   9/2006   DiCarlo ............. A61B 18/1206
                                                           606/41
(Continued)

FOREIGN PATENT DOCUMENTS

JP    H02-36490 Y1    10/1990
JP    H09-75365 A     3/1997
(Continued)

OTHER PUBLICATIONS

Dec. 16, 2014 International Search Report issued in International Application No. PCT/JP2014/079252.
(Continued)

*Primary Examiner* — Ronald Hupczey, Jr.
*Assistant Examiner* — Bo Ouyang
(74) *Attorney, Agent, or Firm* — Oliff PLC

(57) ABSTRACT

A treatment system comprises a first power supply apparatus and a second power supply apparatus each connectable with a surgical device and a neutral electrode, the first power supply apparatus being electrically connected with the second power supply apparatus, the treatment system treating a living tissue while performing transmission and reception of information between the first and second power supply apparatuses, wherein, in a case where the neutral electrode is connected to only one of the first and second power supply apparatuses, an output of the surgical device connected to the second power supply apparatus is inhibited during an output of the surgical device connected to the first power supply apparatus, and the output of the surgical device connected to the first power supply apparatus is inhibited during the output of the surgical device connected to the second power supply apparatus.

6 Claims, 7 Drawing Sheets

(51) Int. Cl.
*A61B 18/14* (2006.01)
*A61B 18/00* (2006.01)

(52) U.S. Cl.
CPC ..... *A61B 18/16* (2013.01); *A61B 2018/00708* (2013.01); *A61B 2018/00773* (2013.01); *A61B 2018/124* (2013.01); *A61B 2018/1273* (2013.01); *A61B 2018/1293* (2013.01); *A61B 2018/165* (2013.01)

(58) Field of Classification Search
USPC .......................................................... 606/35
See application file for complete search history.

(56) References Cited

U.S. PATENT DOCUMENTS

| | | | | |
|---|---|---|---|---|
| 2007/0161979 | A1* | 7/2007 | McPherson | A61B 18/1233 606/35 |
| 2007/0244478 | A1* | 10/2007 | Bahney | A61B 18/16 606/32 |
| 2011/0178517 | A1 | 7/2011 | Beller et al. | |
| 2011/0306960 | A1* | 12/2011 | Eisele | A61B 18/1206 606/33 |

FOREIGN PATENT DOCUMENTS

| | | |
|---|---|---|
| JP | 2006-519080 A | 8/2006 |
| JP | 2012-504435 A | 2/2012 |
| JP | 2012-516724 A | 7/2012 |

OTHER PUBLICATIONS

Jun. 3, 2015 Office Action issued in Japanese Patent Application No. 2015-515739.

\* cited by examiner

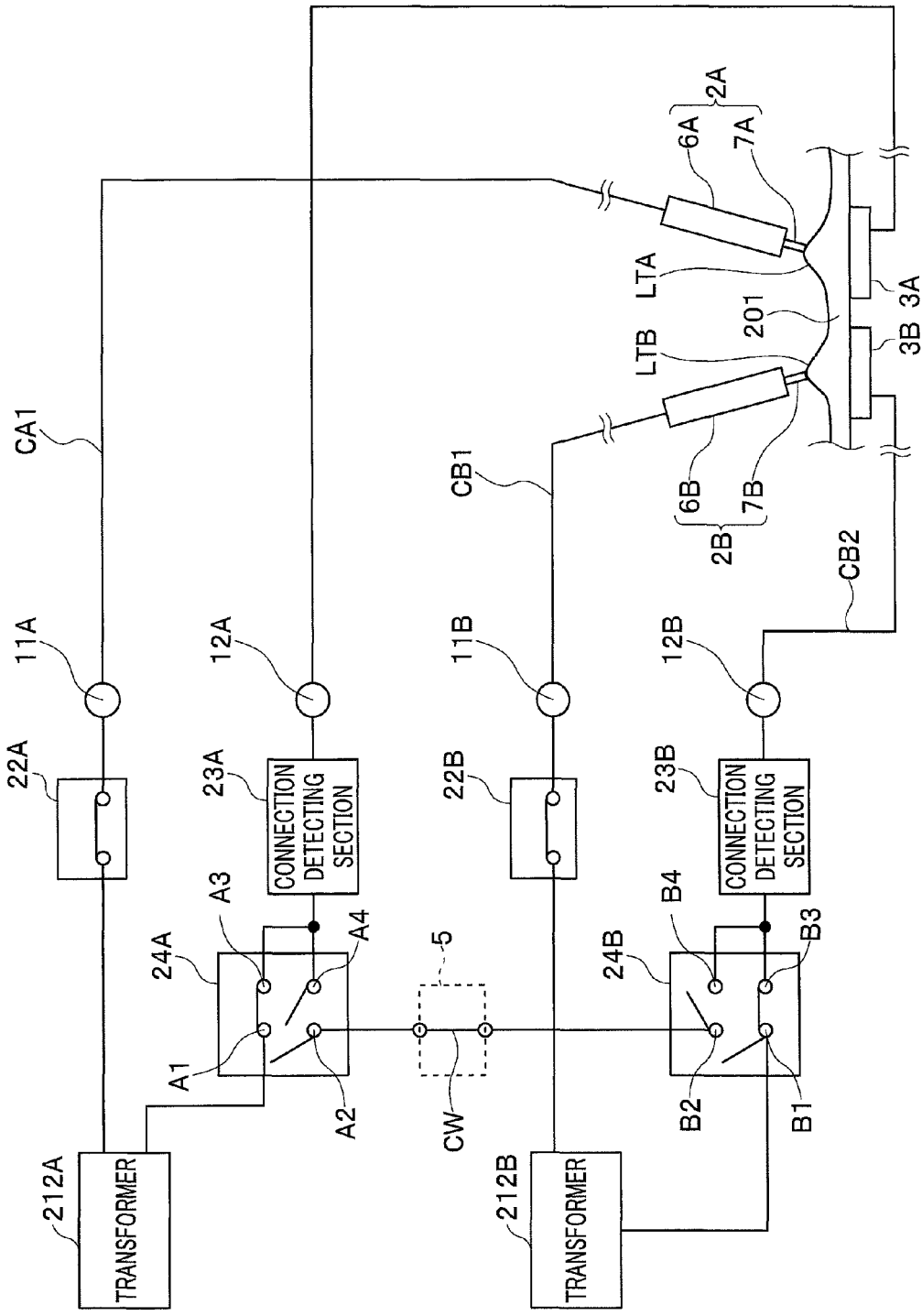

TREATMENT SYSTEM

CROSS REFERENCE TO RELATED APPLICATION

This application is a continuation application of PCT/JP2014/079252 filed on Nov. 4, 2014 and claims benefit of Japanese Application No. 2013-233252 filed in Japan on Nov. 11, 2013, the entire contents of which are incorporated herein by this reference.

BACKGROUND OF THE INVENTION

1. Field of the Invention

The present invention relates to a treatment system, and in particular to a treatment system for performing treatment by applying high-frequency current to a living tissue.

2. Description of the Related Art

An instrument and an apparatus or the like for performing treatment by applying high-frequency current to a living tissue are conventionally known in a medical field.

Specifically, for example, in Japanese Utility-Model Publication No. 2-36490, there is disclosed an electric scalpel apparatus having a configuration capable of performing treatment by applying high-frequency current simultaneously to two regions of a patient to whom one neutral electrode is attached from two scalpel-end electrodes.

SUMMARY OF THE INVENTION

A treatment system according to an aspect of the present invention includes: a first power supply apparatus configured to be connectable with a first electric surgical device and a first neutral electrode; and a second power supply apparatus configured to be connectable with a second electric surgical device and a second neutral electrode, in which the first power supply apparatus and the second power supply apparatus are electrically connected with each other through a connector section and a living tissue is treated while transmission and reception of information is performed between the first power supply apparatus and the second power supply apparatus through a communication section, wherein the first power supply apparatus comprises: a first high-frequency power supply section that supplies high-frequency current to the first electric surgical device based on a first operation instruction signal; a first detecting section that detects whether the first neutral electrode is connected or not; and a first control section that controls the first power supply apparatus, wherein the second power supply apparatus comprises: a second high-frequency power supply section that supplies high-frequency current to the second electric surgical device based on a second operation instruction signal; a second detecting section that detects whether the second neutral electrode is connected or not; and a second control section that controls the second power supply apparatus, wherein, in a case where the first control section and the second control section determine that the first detecting section detects the first neutral electrode and that the second detecting section does not detect the second neutral electrode, through the communication section, the first control section and the second control section perform control to disable supply of the high-frequency current from the second high-frequency power supply section to the second electric surgical device when the first operation instruction signal is inputted to the first high-frequency power supply section, and perform control to disable supply of the high-frequency current from the first high-frequency power supply section to the first electric surgical device when the second operation instruction signal is inputted to the second high-frequency power supply section, and wherein, in a case where the first control section and the second control section determine that the second detecting section detects the second neutral electrode and that the first detecting section does not detect the first neutral electrode, through the communication section, the first control section and the second control section perform control to disable supply of the high-frequency current from the second high-frequency power supply section to the second electric surgical device when the first operation instruction signal is inputted to the first high-frequency power supply section, and perform control to disable supply of the high-frequency current from the first high-frequency power supply section to the first electric surgical device when the second operation instruction signal is inputted to the second high-frequency power supply section.

BRIEF DESCRIPTION OF THE DRAWINGS

FIG. 7 is a diagram for explaining an example, which is different from the examples of FIGS. 3-6, of circuits that are formed when treatments of the living tissues are performed using the treatment system according to the embodiment.

DETAILED DESCRIPTION OF THE PREFERRED EMBODIMENT(S)

Figure 1:
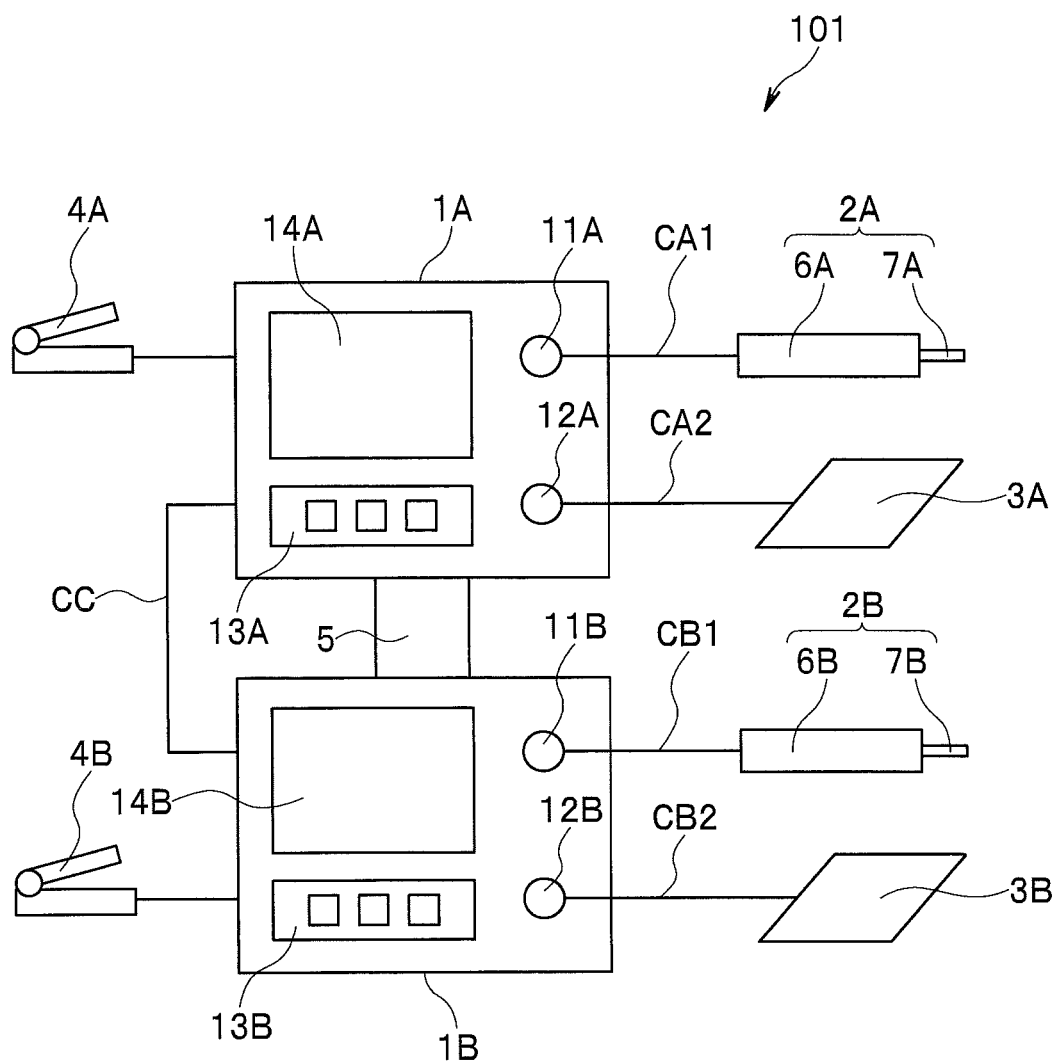
FIG. 1 is a diagram showing a configuration of a principal part of a treatment system according to an embodiment.

Hereinafter, embodiments of the present invention will be described referring to the drawings.

FIG. 1 through FIG. 7 relate embodiments of the present invention. FIG. 1 is a diagram showing a configuration of a principal part of a treatment system according to the embodiment.

As shown in FIG. 1, a treatment system 101 is configured to include a power supply apparatus (first power supply apparatus) 1A and a power supply apparatus (second power supply apparatus) 1B, a treatment instrument (first electric surgical device) 2A and a treatment instrument (second electric surgical device) 2B, and a neutral electrode (first neutral electrode) 3A and a neutral electrode (second neutral electrode) 3B.

The power supply apparatuses 1A and 1B are configured to be electrically connectable with each other through a connection member (connector section) 5 constituted by a connector, a cable or the like. Further, the power supply apparatuses 1A and 1B are configured to be capable of mutually transmitting and receiving information through a communication cable CC as a part of a communication section.

As shown in FIG. 1, the power supply apparatus 1A is configured to be electrically connectable with the treatment instrument 2A through a cable CA1 which is connected to a connection terminal 11A, and to be electrically connectable with the neutral electrode 3A through a cable CA2 which is connected to a connection terminal 12A. Further, the power supply apparatus 1A is configured to be capable of turning on and off supply of high-frequency current to the treatment instrument 2A according to an operation of a foot switch 4A. It is noted that a first operation instruction signal is issued when the foot switch 4A is pressed down.

The treatment instrument 2A is configured as a surgical operation device of a mono-polar type such as a high-frequency electric scalpel. Further, the treatment instrument 2A is configured to include a grasping portion 6A to be grasped by a user, and a treatment portion 7A provided on a distal end side of the grasping portion 6A. Furthermore, as showing in FIG. 1, the treatment instrument 2A is configured to be electrically connectable to the power supply apparatus 1A through the cable CA1 extending from a proximal end side of the grasping portion 6A.

The treatment portion 7A has a function of an active electrode, and is configured to be capable of applying the high-frequency current supplied through the cable CA1 to an intended living tissue of a subject as an object of treatment.

The neutral electrode 3A is formed by a metal conductor such as stainless steel, and formed to have a shape capable of being attached to the subject as the object of treatment so as to be in contact with the subject in a large area. Further, the neutral electrode 3A has a function of a return electrode, and is configured to be capable of collecting the high-frequency current applied to the intended living tissue of the subject as the object of treatment.

Figure 2:
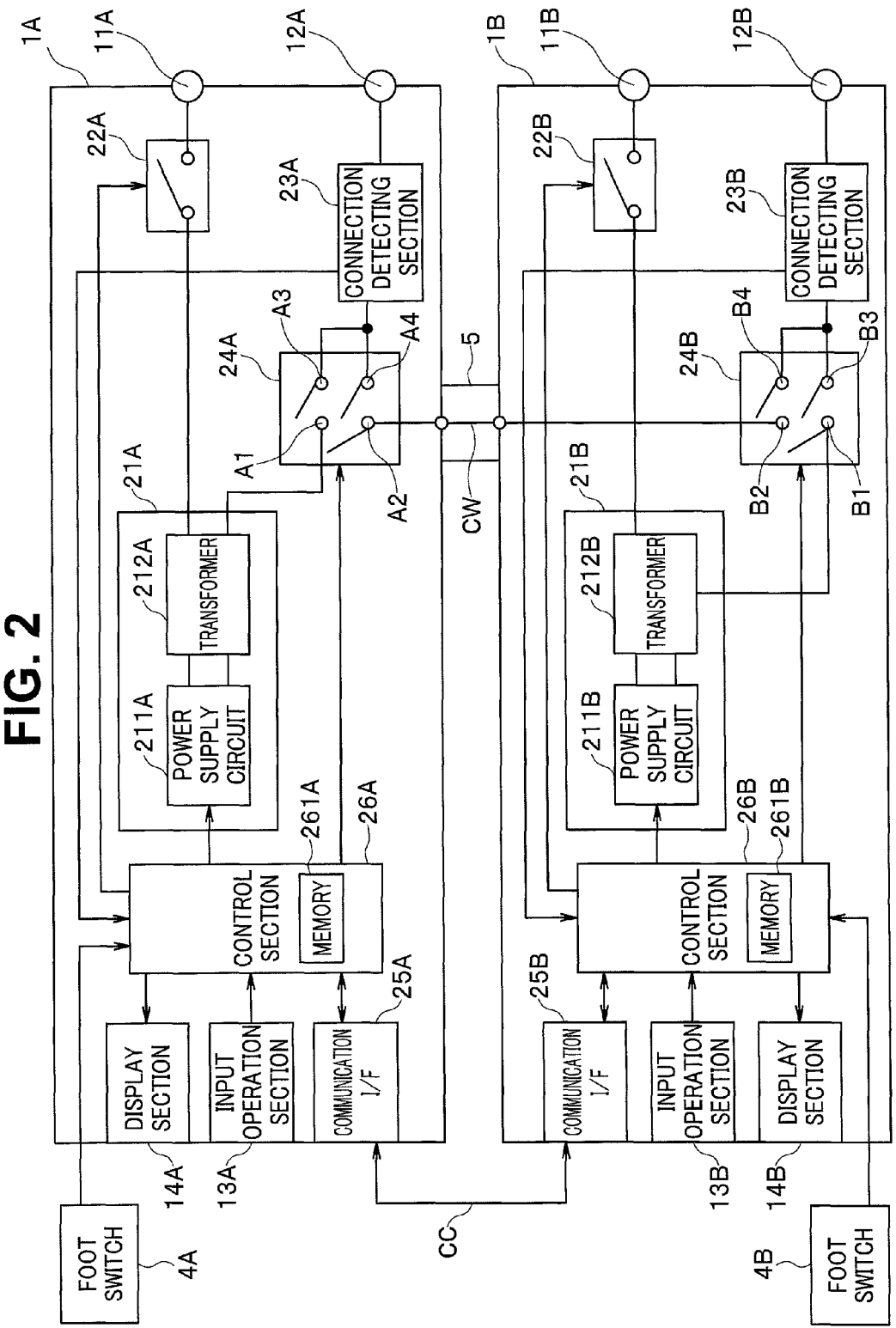
FIG. 2 is a block diagram for explaining an example of internal configurations of power supply apparatuses included in the treatment system according to the embodiment.

As shown in FIG. 1 and FIG. 2, the power supply apparatus 1A is configured to include the connection terminals 11A and 12A, an input operation section 13A, a display section 14A, a high-frequency power supply section (first high-frequency power supply section) 21A, a switch section (third switch section) 22A, a connection detecting section (first detection section) 23A, a switch section (first switch section) 24A, a communication I/F (interface) 25A as a part of a communication section, and a control section (first control section) 26A. FIG. 2 is a block diagram for explaining an example of internal configurations of the power supply apparatuses included in the treatment system according to the embodiment.

The input operation section 13A is configured to include an input interface, such as a switch and/or a button, which is capable of being operated by a user such as a surgeon.

The display section 14A is provided with, for example, an LCD (liquid crystal display), and is configured to be capable of displaying a character string or the like according to control of the control section 26A.

The high-frequency power supply section 21A is configured to include a power supply circuit 211A configured to generate high-frequency power having a frequency in accordance with control of the control section 26A, and a transformer 212A configured to transform the high-frequency power generated by the power supply circuit 211A which is electrically connected to a primary coil (not shown), and to supply high-frequency current in accordance with the transformed high-frequency power to a circuit formed by elements electrically connected to a secondary coil (not shown).

The switch section 22A is provided in a first path that connects between the connection terminal 11A and the high-frequency power supply section 21A. The switch section 22A is configured to include a switch for switching the connection terminal 11A and one end of the secondary coil of the transformer 212A into one of a conducting state and a non-conducting state on the basis of control of the control section 26A.

The connection detecting section 23A is connected at a rear stage of the connection terminal 12A and is configured to be capable of detecting connection or disconnection of the neutral electrode 3A (with the cable CA2) at the connection terminal 12A based on, for example, a detection result of detection of a resistance value (or change in the resistance value) at the connection terminal 12A. Further, the connection detecting section 23A is configured to be capable of generating a connection discrimination signal which is discriminable of the connection or disconnection of the neutral electrode 3A (with the cable CA2) at the connection terminal 12A, and to output the signal to the control section 26A. Further, the connection detecting section 23A is configured to be capable of outputting the high-frequency current which is inputted through the connection terminal 12A to the switch section 24A as it is.

The switch section 24A is configured to include a contact A1 which is connected to the other end of the secondary coil of the transformer 212A, a contact A2 which is connected to a contact B2 (described later) of a switch section 24B through a lead wire CW built in the connection member 5, and contacts A3 and A4 which are connected to the connection detecting section 23A. Further, the switch section 24A is configured to include a switch for switching the contact A1 and the contact A2 into one of a conducting state and a non-conducting state, a switch for switching the contact A1 and the contact A3 into one of a conducting state and a non-conducting state, and a switch for switching the contact A2 and the contact A4 into one of a conducting state and a non-conducting state.

The communication I/F 25A is provided with, for example, a connector (not shown) or the like to which the communication cable CC is detachably connectable, and is configured to be capable of outputting information outputted from the control section 26A to a communication I/F 25B (described later) of the power supply apparatus 1B through the communication cable CC. Further, the communication I/F 25A is configured to be capable of outputting information inputted through the communication cable CC to the control section 26A.

The control section 26A is configured to include a memory 261A in which at least information concerning at least one of magnitude of the high-frequency current (e.g. maximum rated current), magnitude of high-frequency voltage (e.g. maximum rated voltage), magnitude of power (e.g. maximum rated power) indicative of energy capable of being supplied from the high-frequency power supply section 21A is stored as inherent information concerning the power supply apparatus 1A. Further, the control section 26A is configured to be capable of outputting information read from the memory 261A to the communication I/F 25A.

The control section 26A is configured to be capable of generating information capable of discriminating whether or not the neutral electrode 3A is presently connected to the power supply apparatus 1A, based on the connection discrimination signal outputted from the connection detecting section 23A, and outputting the generated information to the communication I/F 25A.

The control section 26A is configured to be capable of performing control in accordance with an operation of the input operation section 13A. Specifically, the control section 26A is configured to be capable of performing control of the high-frequency power supply section 21A to generate, when, for example, a frequency setting switch (not shown) provided at the input operation section 13A is operated, high-frequency power having a frequency set by the frequency setting switch.

Further, the control section 26A is configured to be capable of performing control for causing the display section 14A to display a predetermined character string based on the connection discrimination signal outputted from the connection detecting section 23A and the information outputted from the communication I/F 25A.

The control section 26A is configured to turn on the supply of the high-frequency current to the treatment instrument 2A by making the switch section 22A be in the conducting state in accordance with an operation of the foot switch 4A. Further, the control section 26A is configured to turn off the supply of the high-frequency current to the treatment instrument 2A by making the switch section 22A be in the non-conducting state in accordance with an operation of the foot switch 4A. Furthermore, the control section 26A is configured to capable of generating information capable of discriminating whether or not the high-frequency current is presently supplied to the treatment instrument 2A based on the operation state of the foot switch 4A, and outputting the generated information to the communication I/F 25A.

The control section 26A is configured to perform control concerning switching of the respective switches of the switch section 24A as the first switch section based on the connection discrimination signal outputted from the connection detecting section 23A and the information outputted from the communication I/F 25A. Further, the control section 26A is configured to perform control concerning switching of the switch section 22A as the third switch section based on the operation instruction signal (first operation instruction signal) of the foot switch 4A.

On the other hand, the power supply apparatus 1B is configured to be electrically connectable with the treatment instrument 2B through a cable CB1 connected to a connection terminal 11B, and to be electrically connectable with the neutral electrode 3B through a cable CB2 connected to a connection terminal 12B. Further, the power supply apparatus 1B is configured to be capable of turning on and off supply of high-frequency current to the treatment instrument 2B in accordance with an operation of the foot switch 4B. It is noted that a second operation instruction signal is issued when the foot switch 4B is pressed down.

The treatment instrument 2B is configured as a surgical operation device of a mono-polar type such as a high-frequency electric scalpel. Further, the treatment instrument 2B is configured to include a grasping portion 6B to be grasped by a user, and a treatment portion 7B provided on a distal end side of the grasping portion 6B. Furthermore, as showing in FIG. 1, the treatment instrument 2B is configured to be electrically connectable to the power supply apparatus 1B through the cable CB1 extending from a proximal end side of the grasping portion 6B.

The treatment portion 7B has a function of an active electrode, and is configured to be capable of applying high-frequency current supplied through the cable CB1 to an intended living tissue of the subject as the object of treatment.

The neutral electrode 3B is formed by a metal conductor such as stainless steel, and formed to have a shape capable of being attached to the subject as the object of treatment so as to be in contact with the subject in a large area. Further, the neutral electrode 3B has a function of a return electrode, and is configured to be capable of collecting the high-frequency current applied to the intended living tissue of the subject as the object of treatment.

As shown in FIG. 1 and FIG. 2, the power supply apparatus 1B is configured to include the connection terminals 11B and 12B, an input operation section 13B, a display section 14B, a high-frequency power supply section (second high-frequency power supply section) 21B, a switch section (fourth switch section) 22B, a connection detecting section (second detecting section) 23B, the switch section (second switch section) 24B, the communication I/F (interface) 25B as a part of the communication section, and a control section (second control section) 26B.

The input operation section 13B is configured to include an input interface, such as a switch and/or a button, which is capable of being operated by a user such as a surgeon.

The display section 14B is provided with, for example, an LCD (liquid crystal display), and is configured to be capable of displaying a character string or the like according to control of the control section 26B.

The high-frequency power supply section 21B is configured to include a power supply circuit 211B configured to generate high-frequency power having a frequency in accordance with control of the control section 26B, and a transformer 212B configured to transform the high-frequency power generated by the power supply circuit 211B which is electrically connected to a primary coil (not shown), and to supply high-frequency current in accordance with the transformed high-frequency power to a circuit formed by elements electrically connected to a secondary coil (not shown).

The switch section 22B is provided in a second path that connects between the connection terminal 11B and the high-frequency power supply section 21B. The switch section 22B is configured to include a switch for switching the connection terminal 11B and one end of the secondary coil of the transformer 212B into one of a conducting state and a non-conducting state on the basis of control of the control section 26B.

The connection detecting section 23B is connected at a rear stage of the connection terminal 12B, and is configured to capable of detecting connection or disconnection of the neutral electrode 3B (with the cable CB2) at the connection terminal 12B based on, for example, a detection result of detection of a resistance value (or change in the resistance value) at the connection terminal 12B. Further, the connection detecting section 23B is configured to be capable of generating a connection discrimination signal which is discriminable of the connection or disconnection of the neutral electrode 3B (with the cable CB2) at the connection terminal 12B, and to output the signal to the control section 26B. Furthermore, the connection detecting section 23B is configured to capable of outputting the high-frequency current which is inputted through the connection terminal 12B to the switch section 24B as it is.

The switch section 24B is configured to include a contact B1 which is connected to the other end of the secondary coil of the transformer 212B, a contact B2 which is connected to the contact A2 of the switch section 24A through the lead wire CW built in the connection member 5, and contacts B3 and B4 which are connected to the connection detecting section 23B. Further, the switch section 24B is configured to include a switch for switching the contact B1 and the contact B2 into one of a conducting state and a non-conducting state, a switch for switching the contact B1 and the contact B3 into one of a conducting state and a non-conducting state, and a switch for switching the contact B2 and the contact B4 into one of a conducting state and a non-conducting state.

The communication I/F 25B is provided with, for example, a connector (not shown) to which the communication cable CC is detachably connectable, and is configured to be capable of outputting information outputted from the control section 26B to the communication I/F 25A of the power supply apparatus 1A through the communication cable CC. Further, the communication I/F 25B is configured to be capable of outputting information inputted through the communication cable CC to the control section 26B.

The control section 26B is configured to include a memory 261B in which at least information concerning at least one of magnitude of the high-frequency current (e.g. maximum rated current), magnitude of high-frequency voltage (e.g. maximum rated voltage), magnitude of power (e.g. maximum rated power) indicative of energy capable of being supplied from the high-frequency power supply section 21B is stored as inherent information concerning the power supply apparatus 1B. Further, the control section 26B is configured to be capable of outputting information read from the memory 261B to the communication I/F 25B.

The control section 26B is configured to be capable of generating information capable of discriminating whether or not the neutral electrode 3B is presently connected to the power supply apparatus 1B, based on the connection discrimination signal outputted from the connection detecting section 23B, and outputting the generated information to the communication I/F 25B.

The control section 26B is configured to be capable of performing control in accordance with an operation of the input operation section 13B. Specifically, the control section 26B is configured to be capable of performing control of the high-frequency power supply section 21B to generate, when, for example, a frequency setting switch (not shown) provided at the input operation section 13B is operated, high-frequency power having a frequency set by the frequency setting switch.

Further, the control section 26B is configured to be capable of performing control for causing the display section 14B to display a predetermined character string based on the connection discrimination signal outputted from the connection detection section 23B and the information outputted from the communication I/F 25B.

The control section 26B is configured to turn on the supply of the high-frequency current to the treatment instrument 2B by making the switch section 22B be in the conducting state in accordance with an operation of the foot switch 4B. Further, the control section 26B is configured to turn off the supply of the high-frequency current to the treatment instrument 2B by making the switch section 22B be in the non-conducting state in accordance with an operation of the foot switch 4B. Furthermore, the control section 26B is configured to capable of generating information capable of discriminating whether or not the high-frequency current is presently supplied to the treatment instrument 2B based on the operation state of the foot switch 4B, and outputting the generated information to the communication I/F 25B.

The control section 26B is configured to perform control concerning switching of the respective switches of the switch section 24B as the second switch section based on the connection discrimination signal outputted from the connection detection section 23B and the information outputted from the communication I/F 25B. Further, the control section 26B is configured to perform control concerning switching of the switch section 22B as the fourth switch section based on the operation instruction signal (second operation instruction signal) of the foot switch 4B.

Thus, according to the configuration of the treatment system 101 as described above, it is possible to transmit and receive the information concerning the connection and disconnection of the neutral electrodes 3A and 3B, the information concerning the supply and non-supply of the high-frequency current to the treatment instruments 2A and 2B, and the information concerning magnitude of the high-frequency current capable of being supplied from the high-frequency power supply sections 21A and 21B, and to share various pieces of information transmitted through the communication cable CC by the control sections 26A and 26B.

Besides, according to the treatment system 101 of the present embodiment, not limited to a system having the configuration that the communication I/Fs 25A and 25B perform wire communication through the communication cable CC, the system may have a configuration that the communication I/Fs 25A and 25B perform wireless communication by wireless signals.

Subsequently, an operation of the treatment system 101 having the above-described configuration will be described.

First, in a state where the treatment instrument 2A and the foot switch 4A are connected to the power supply apparatus 1A, the treatment instrument 2B and the foot switch 4B are connected to the power supply apparatus 1B, the communication I/Fs 25A and 25B are connected to each other by the communication cable CC, and the switches 24A and 23B are connected to each other by the connection member (connector section) 5, the user turns on main switches (not shown) provided at the input operation sections 13A and 13B to thereby start up the power supply apparatuses 1A and 1B. Besides, it is assumed that the supply of the high-frequency current from the power supply apparatus 1A to the treatment instrument 2A, and the supply of the high-frequency current from the power supply apparatus 1B to the treatment instrument 2B are not performed at timing immediately after the power supply apparatuses 1A and 1B are started.

The control section 26A generates information indicating that the high-frequency current is not presently provided to the treatment instrument 2A when the power supply apparatus 1A is started, and outputs the generated information to the power supply apparatus 1B through the communication cable CC. Further, the control section 26A reads the information stored in the memory 261A when the power supply apparatus 1A is started, and outputs the read information to the power supply apparatus 1B through the communication cable CC.

The control section 26B generates information indicating that the high-frequency current is not presently provided to the treatment instrument 2B when the power supply apparatus 1B is started, and outputs the generated information to the power supply apparatus 1A through the communication cable CC. Further, the control section 26B reads the information stored in the memory 261B when the power supply apparatus 1B is started, and outputs the read information to the power supply apparatus 1A through the communication cable CC.

On the other hand, the user, after starting the power supply apparatuses 1A and 1B, electrically connects one of the neutral electrode 3A and the neutral electrode 3B to one of the power supply apparatus 1A and the power supply apparatus 1B.

Here, operations, etc. of respective parts in a case where the neutral electrode 3A is connected to the power supply apparatus 1A before the neutral electrode 3B is connected of the power supply apparatus 1B will be described.

The connection detecting section 23A detects that the neutral electrode 3A (with the cable CA2) is connected to the connection terminal 12A based on the detection result of detection of the resistance value (or change in the resistance value) at the connection terminal 12A. Then, the connection detecting section 23A generates the connection discrimination signal indicating that the neutral electrode 3A (with the cable CA2) is connected to the connection terminal 12A, and outputs the signal to the control section 26A.

The control section 26A generates information indicating that the neutral electrode 3A is presently connected to the power supply apparatus 1A based on the connection discrimination signal outputted from the connection detecting section 23A, and outputs the generated information to the power supply apparatus 1B through the communication cable CC.

The control section 26B performs control for maintaining the non-conducting state between the contact B1 and the contact B3 of the switch section 24B and for maintaining the non-conducting state between the contact B2 and the contact B4 of the switch section 24B in a period in which the neutral electrode 3A is connected to the power supply apparatus 1A, based on information outputted from the communication I/F 25B.

On the other hand, the user, after attaching the neutral electrode 3A to the subject as the object of treatment, in a state where the treatment portion 7A is brought into contact with the intended living tissue of the subject, operates the foot switch 4A and thereby the first operation instruction signal is outputted from the foot switch 4A. Thereby, the control section 26A detects the first operation instruction signal and issues an instruction to cause the high-frequency power supply section 21A to supply the high-frequency current to the treatment instrument 2A. That is, based on the first operation instruction signal from the foot switch 4A, the high-frequency power supply section 21A supplies the high-frequency current to the treatment instrument 2A.

Further, when the control section 26A detects the first operation instruction signal for starting the supply of the high-frequency current to the treatment instrument 2A, the control section 26A performs control for making the switch section 22A be in the conducting state, performs control for making the contact A1 and the contact A3 of the switch section 24A be in conducting state, and performs control for making the contact A2 and the contact A4 of the switch section 24A be in the non-conducting state, and generates information indicating that the high-frequency current is presently supplied to the treatment instrument 2A, and outputs the generated information to the power supply apparatus 1B through the communication cable CC.

The control section 26B performs control for maintaining the non-conducting state of the switch section 22B in a period in which the high-frequency current is supplied to the treatment instrument 2A (in a period in which the first operation instruction signal is outputted) based on information outputted from the communication I/F 25B.

That is, according to the operations of the respective parts as described above, in a period in which the neutral electrode 3A is connected to the power supply apparatus 1A and the high-frequency current is supplied to the treatment instrument 2A, for example, even if the neutral electrode 3B (with the cable CB2) is further connected to the connection terminal 12B, the high-frequency current does not flow forward from the switch section 24B (to the secondary side of the transformer 212A and the secondary side of the transformer 212B), and therefore the function of the neutral electrode 3B as the return electrode can be disabled.

Further, according to the operations of the respective parts as described above, in the period in which the neutral electrode 3A is connected to the power supply apparatus 1A and the high-frequency current is supplied to the treatment instrument 2A, for example, even in a case where an operation for starting the supply of the high-frequency current to the treatment instrument 2B is performed on the foot switch 4B, the high-frequency current does not flow forward from the switch section 22B, and therefore the function of the treatment instrument 2B as the active electrode can be disabled.

Figure 3:
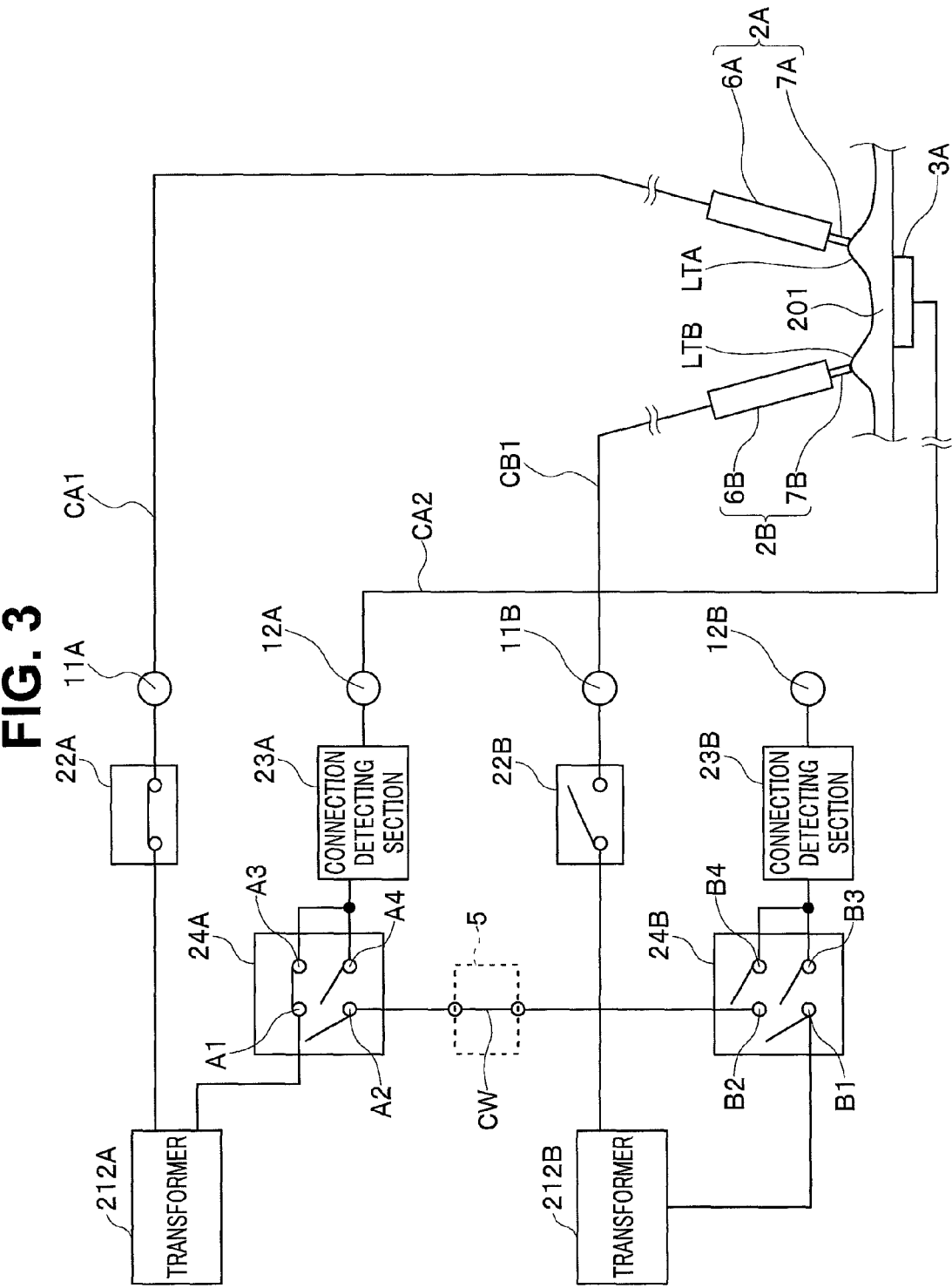
FIG. 3 is a diagram for explaining an example of a circuit that is formed when a treatment of a living tissue is performed using the treatment system according to the embodiment.

Furthermore, according to the operations of the respective parts as described above, in the state where the neutral electrode 3A is connected to the power supply apparatus 1A and the treatment portion 7A is in contact with the intended living tissue LTA of the subject, a circuit CP1 including a current flowing path (the transformer 212A→the switch section 22A→(the connection terminal 11A→the cable CA1→) the treatment portion 7A→the living tissue LTA→the subject 201→the neutral electrode 3A→(the cable CA2→the connection terminal 12A→) the connection detecting section 23A→the switch section 24A→the transformer 212A) shown in FIG. 3 is formed as an example. Therefore, in the state where the neutral electrode 3A is attached to the subject 201, the treatment of the living tissue LTA can be performed by applying the high-frequency current from the treatment section 7A to the living tissue LTA. FIG. 3 is a diagram for explaining an example of the circuit faulted when the treatment of the living tissue is performed using the treatment system according to the embodiment.

On the other hand, the user, after attaching the neutral electrode 3A to the subject as the object of the treatment, in a state in which the treatment portion 7B is brought into contact with the intended living tissue of the subject, operates the foot switch 4B and thereby the second operation instruction signal is outputted from the foot switch 4B. Thereby, the control section 26B detects the second operation instruction signal and issues an instruction to cause the high-frequency power supply section 21B to supply the high-frequency current to the treatment instrument 2B. That is, based on the second operation instruction signal form the foot switch 4B, the high-frequency power supply section 21B supplies the high-frequency current to the treatment instrument 2B.

Further, when the control section 26B detects the second operation instruction signal for starting the supply of the high-frequency current to the treatment instrument 2B, the control section 26B performs control for making the switch section 22B be in the conducting state, performs control for making the contact B1 and the contact B2 of the switch section 24B be in conducting state, and generates information indicating that the high-frequency current is presently supplied to the treatment instrument 2B, and outputs the generated information to the power supply apparatus 1A through the communication cable CC.

The control section 26A performs control for maintaining the non-conducting state of the switch section 22A and performs control for making the contact A2 and the contact A4 of the switch section 24A be in the conducting state in a period in which the high-frequency current is supplied to the treatment instrument 2B, based on the information outputted from the communication I/F 25A.

That is, according to the operations of the respective parts as described above, in a period in which the neutral electrode 3A is connected to the power supply apparatus 1A and the high-frequency current is supplied to the treatment instrument 2B (the second operation instruction signal is outputted), for example, even if the neutral electrode 3B (with the cable CB2) is further connected to the connection terminal 12B, the high-frequency current does not flow forward from the switch section 24B (to the secondary side of the transformer 212A and the secondary side of the transformer 212B), and therefore the function of the neutral electrode 3B as the return electrode can be disabled.

Further, according to the operations of the respective parts as described above, in the period in which the neutral electrode 3A is connected to the power supply apparatus 1A and the high-frequency current is supplied to the treatment instrument 2B, for example, even in a case where an operation for starting the supply of the high-frequency current to the treatment instrument 2A is performed on the foot switch 4A, the high-frequency current does not flow forward from the switch section 22A, and therefore the function of the treatment instrument 2A as the active electrode can be disabled.

Figure 4:
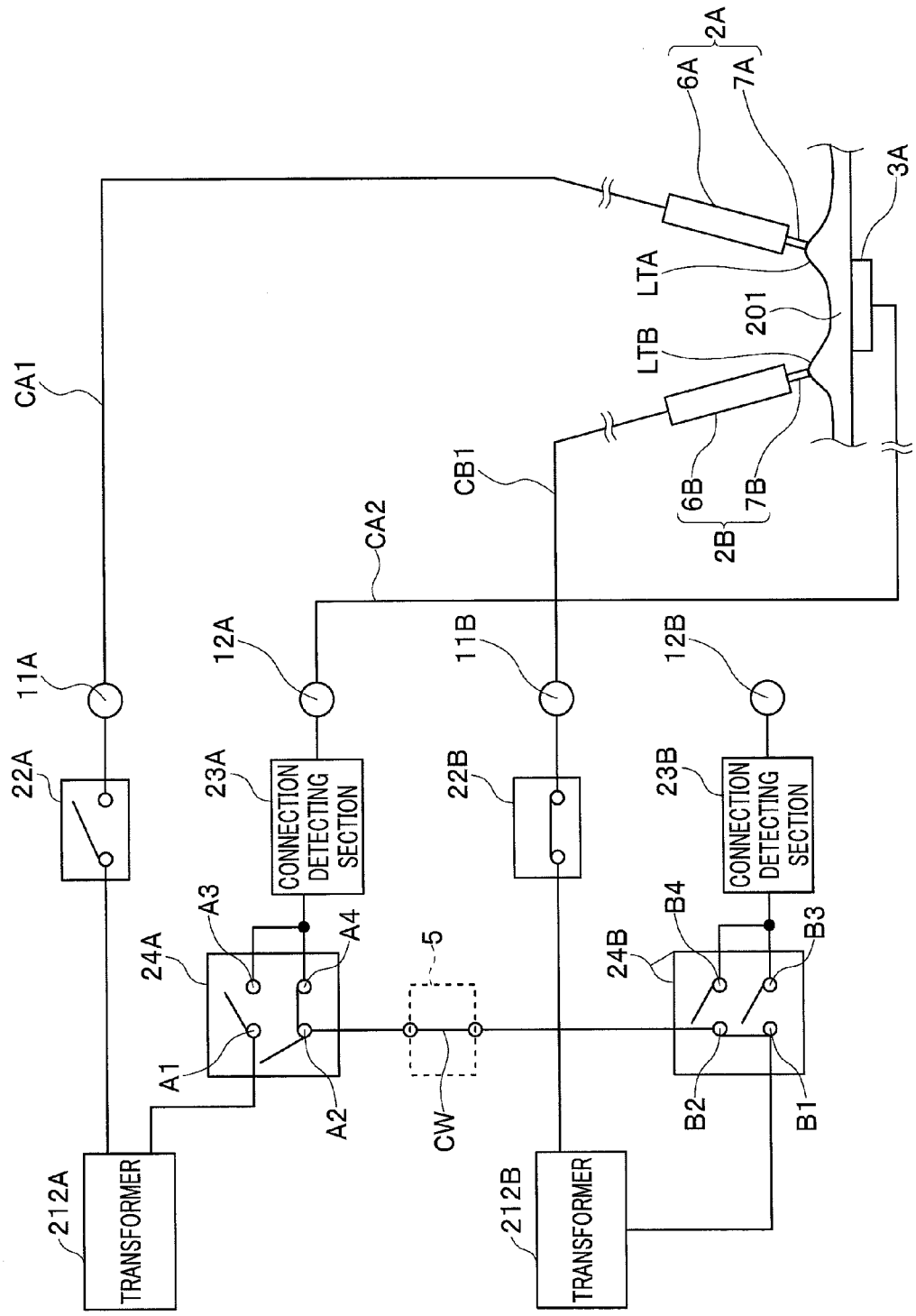
FIG. 4 is a diagram for explaining an example, which is different from the example of FIG. 3, of a circuit that is formed when a treatment of the living tissue is performed using the treatment system according to the embodiment.

According to the operations of the respective parts as described above, in the period in which the neutral electrode 3A is connected to the power supply apparatus 1A and the treatment section 7B is in contact with the intended living tissue LTB of the subject, a circuit CP2 including a current flowing path (the transformer 212B→the switch section 22B→(the connection terminal 11B→the cable CB1→) the treatment portion 7B→the living tissue LTB→the subject 201→the neutral electrode 3A→(the cable CA2→the connection terminal 12A→) the connection detecting section 23A→the switch section 24A (the lead wire CW of) the connection member 5→the switch section 24B→the transformer 212B) shown in FIG. 4 is formed as an example. Therefore, in the state where the neutral electrode 3A is attached to the subject 201, the treatment of the living tissue LTB can be performed by applying the high-frequency current from the treatment portion 7B to the living tissue LTB. FIG. 4 is a diagram for explaining an example, which is different from the example of FIG. 3, of the circuit formed when a treatment of the living tissue is performed using the treatment system according to the embodiment.

Besides, the control section 26B of the present embodiment may be configured to perform control for causing the display section 14B to display a predetermined character string or the like that is capable of notify that the neutral electrode 3B is erroneously connected, when it is detected that the neutral electrode 3B is connected to the power supply apparatus 1B after detecting that the neutral electrode 3A is connected to the power supply apparatus 1A based on the information outputted from the communication I/F 25B and the connection discrimination signal outputted from the connection detecting section 23B.

Next, operations, etc. of the respective parts in a case where the neutral electrode 3B is connected to the power supply apparatus 1B before the neutral electrode 3A is connected to the power supply apparatus 1A will be described.

The connection detecting section 23B detects that the neutral electrode 3B (with the cable CB2) is connected to the connection terminal 12B based on the detection result of detection of the resistance value (or change in the resistance value) at the connection terminal 12B. Then, the connection detecting section 23B generates the connection discrimination signal indicating that the neutral electrode 3B (with the cable CB2) is connected to the connection terminal 12B, and outputs the signal to the control section 26B.

The control section 26B generates information indicating that the neutral electrode 3B is presently connected to the power supply apparatus 1B based on the connection discrimination signal outputted from the connection detecting section 23B, and outputs the generated information to the power supply apparatus 1A through the communication cable CC.

The control section 26A performs control for maintaining the non-conducting state between the contact A1 and the contact A3 of the switch section 24A and for maintaining the non-conducting state between the contact A2 and the contact A4 of the switch section 24A in a period in which the neutral electrode 3B is connected to the power supply apparatus 1B, based on the information outputted from the communication I/F 25A.

On the other hand, the user, after attaching the neutral electrode 3B to the subject as the object of treatment, in a state where the treatment portion 7B is brought into contact with the intended living tissue of the subject, operates the foot switch 4B to thereby start the supply of the high-frequency current to the treatment instrument 2B.

When the control section 26B detects the operation of the foot switch 4B for starting the supply of the high-frequency current to the treatment instrument 2B, the control section 26B performs control for making the switch section 22B be in the conducting state, performs control for making the contact B1 and the contact B3 of the switch section 24B be in conducting state, and performs control for making the contact B2 and the contact B4 of the switch section 24B be in the non-conducting state, and generates information indicating that the high-frequency current is presently supplied to the treatment instrument 2B, and outputs the generated information to the power supply apparatus 1A through the communication cable CC.

The control section 26A performs control for maintaining the non-conducting state of the switch section 22A in a period in which the high-frequency current is supplied to the treatment instrument 2B based on information outputted from the communication I/F 25A.

That is, according to the operations of the respective parts as described above, in a period in which the neutral electrode 3B is connected to the power supply apparatus 1B and the high-frequency current is supplied to the treatment instrument 2B, for example, even if the neutral electrode 3A (with the cable CA2) is further connected to the connection terminal 12A, the high-frequency current does not flow forward from the switch section 24A (to the secondary side of the transformer 212A and the secondary side of the transformer 212B), and therefore the function of the neutral electrode 3A as the return electrode can be disabled.

Further, according to the operations of the respective parts as described above, in the period in which the neutral electrode 3B is connected to the power supply apparatus 1B and the high-frequency current is supplied to the treatment instrument 2B, for example, even in a case where an operation for starting the supply of the high-frequency current to the treatment instrument 2A is performed on the foot switch 4A, the high-frequency current does not flow forward from the switch section 22A, and therefore the function of the treatment instrument 2A as the active electrode can be disabled.

Figure 5:
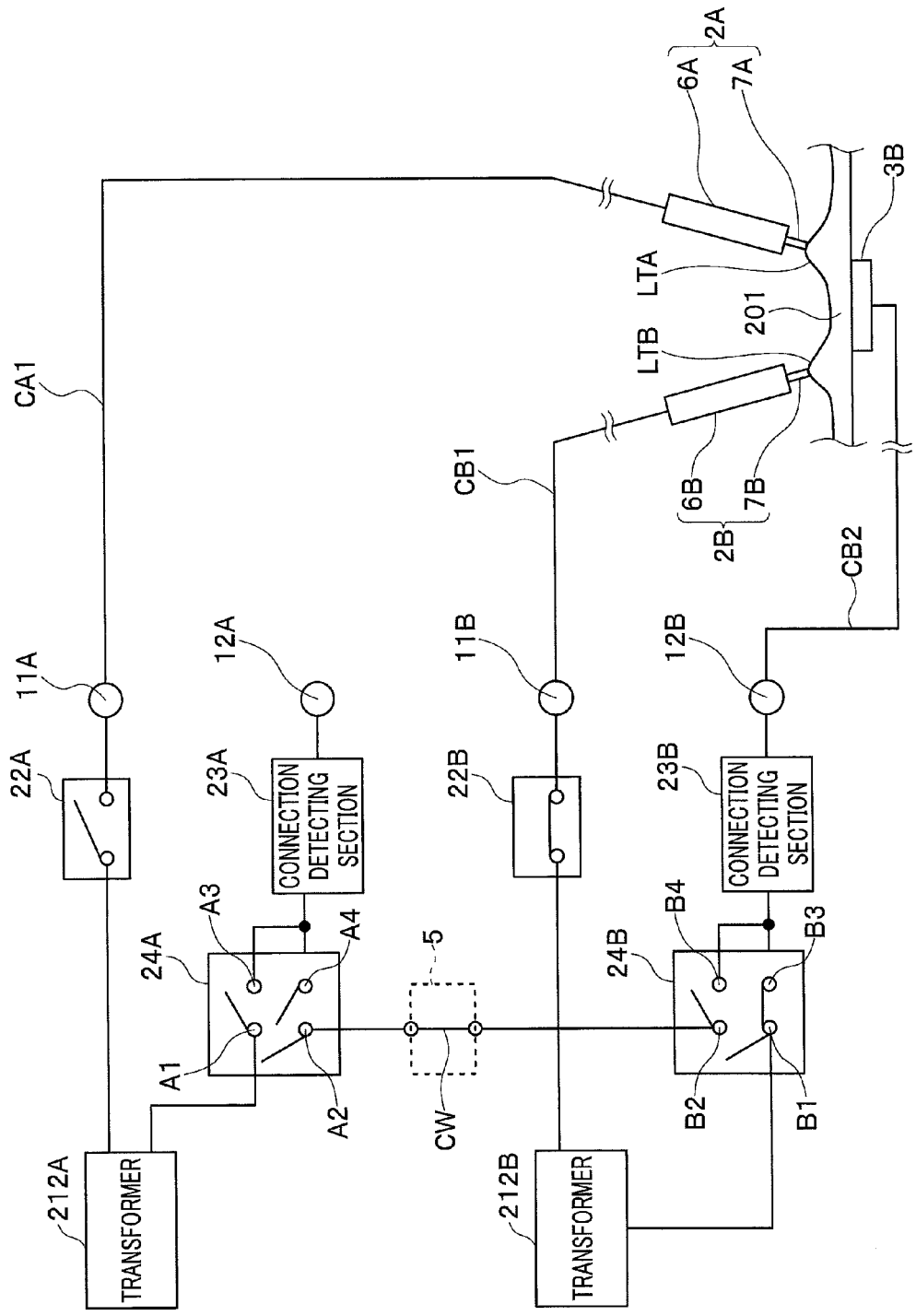
FIG. 5 is a diagram for explaining an example, which is different from the examples of FIGS. 3 and 4, of a circuit that is formed when a treatment of the living tissue is performed using the treatment system according to the embodiment.

Furthermore, according to the operations of the respective parts as described above, in the period in which the neutral electrode 3B is connected to the power supply apparatus 1B and the treatment section 7B is in contact with the intended living tissue LTB of the subject, a circuit CP3 including a current flowing path (the transformer 212B→the switch section 22B→(the connection terminal 11B→the cable CB1→) the treatment portion 7B→the living tissue LTB→the subject 201→the neutral electrode 3B→(the cable CB2→the connection terminal 12B→) the connection detecting section 23B→the switch section 24B→the transformer 212B) shown in FIG. 5 is formed as an example. Therefore, in the state where the neutral electrode 3B is attached to the subject 201, the treatment of the living tissue LTB can be performed by applying the high-frequency current from the treatment section 7B to the living tissue LTB. FIG. 5 is a diagram for explaining an example, which is different from the examples of FIGS. 3 and 4, of the circuit formed when a treatment of the living tissue is performed using the treatment system according to the embodiment.

On the other hand, the user, after attaching the neutral electrode 3B to the subject as the object of the treatment, in a state in which the treatment section 7A is brought into contact with the intended living tissue of the subject, operates the foot switch 4A to thereby start the supply of the high-frequency current to the treatment instrument 2A.

Further, when the control section 26A detects the operation of the foot switch 4A for starting the supply of the high-frequency current to the treatment instrument 2A, the control section 26A performs control for making the switch section 22A be in the conducting state, performs control for making the contact A1 and the contact A2 of the switch section 24A be in conducting state, and generates information indicating that the high-frequency current is presently supplied to the treatment instrument 2A, and outputs the generated information to the power supply apparatus 1B through the communication cable CC.

The control section 26B performs control for maintaining the non-conducting state of the switch section 22B and performs control for making the contact B2 and the contact B4 of the switch section 24B be in the conducting state in a period in which the high-frequency current is supplied to the treatment instrument 2A, based on the information outputted from the communication OF 25B.

That is, according to the operations of the respective parts as described above, in a period in which the neutral electrode 3B is connected to the power supply apparatus 1B and the high-frequency current is supplied to the treatment instrument 2A, for example, even if the neutral electrode 3A (with the cable CA2) is further connected to the connection terminal 12A, the high-frequency current does not flow forward from the switch section 24A (to the secondary side of the transformer 212A and the secondary side of the transformer 212B), and therefore the function of the neutral electrode 3A as the return electrode can be disabled.

Further, according to the operations of the respective parts as described above, in the period in which the neutral electrode 3B is connected to the power supply apparatus 1B and the high-frequency current is supplied to the treatment instrument 2A, for example, even in a case where an operation for starting the supply of the high-frequency current to the treatment instrument 2B is performed on the foot switch 4B, the high-frequency current does not flow forward from the switch section 22B, and therefore the function of the treatment instrument 2B as the active electrode can be disabled.

Figure 6:
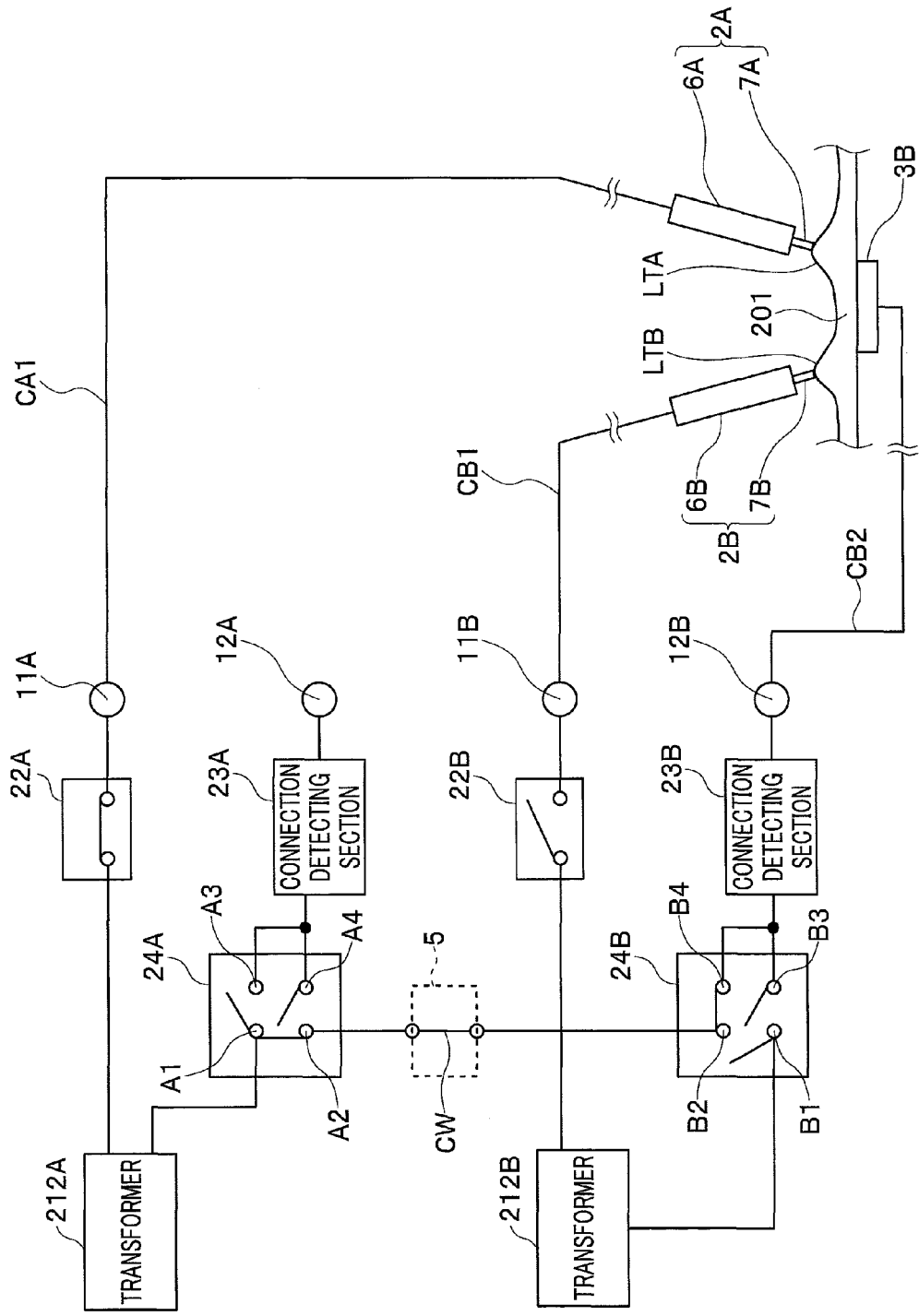
FIG. 6 is a diagram for explaining an example, which is different from the examples of FIGS. 3-5, of a circuit that is formed when a treatment of the living tissue is performed using the treatment system according to the embodiment.

According to the operations of the respective parts as described above, in the period in which the neutral electrode 3B is connected to the power supply apparatus 1B and the treatment section 7A is in contact with the intended living tissue LTA of the subject, a circuit CP4 including a current flowing path (the transformer 212A→the switch section 22A→(the connection terminal 11A→the cable CA1→) the treatment portion 7A→the living tissue LTA→the subject 201→the neutral electrode 3B→(the cable CB2→the connection terminal 12B→) the connection detecting section 23B→the switch section 24B→(the lead wire CW of) the connection member 5→the switch section 24A→the transformer 212A) shown in FIG. 6 is formed as an example. Therefore, in the state where the neutral electrode 3B is attached to the subject 201, the treatment of the living tissue LTA can be performed by applying the high-frequency current from the treatment section 7A to the living tissue LTA. FIG. 6 is a diagram for explaining an example, which is different from the examples of FIGS. 3-5, of the circuit formed when a treatment of the living tissue is performed using the treatment system according to the embodiment.

As described above, according to the present embodiment, the operation is performed such that only one neutral electrode (the neutral electrode 3A or 3B) which is connected to the power supply apparatus earlier than the other neutral electrode performs the function as the return electrode while inhibiting the high-frequency current from being simultaneously applied from the treatment instruments 2A and 2B. Therefore, according to the present embodiment, an application state of the high-frequency current to the intended living tissue as the object of treatment is stabilized, and the treatment with respect to the intended living tissue can be appropriately performed.

Besides, the control section 26A of the present embodiment may be configured to perform control for causing the display section 14A to display a predetermined character string or the like that is capable of notifying that the neutral electrode 3A is erroneously connected, when it is detected that the neutral electrode 3A is connected to the power supply apparatus 1A after detecting that the neutral electrode 3B is connected to the power supply apparatus 1B based on the information outputted from the communication I/F 25A and the connection discrimination signal outputted from the connection detecting section 23A.

On the other hand, according to the present embodiment, not limited to the configuration in which the above-described operation is performed, for example, it may be configured such that the control sections 26A and 26B shares information concerning a comparison result of comparison between a magnitude of the high-frequency current which can be supplied from the high-frequency power supply 21A and a magnitude of the high-frequency current which can be supplied from the high-frequency power supply 21B based on the information stored in the memories 261A and 261B, and the operation is performed in accordance with the comparison result.

Specifically, for example, when information that the magnitude of the high-frequency current which can be supplied from the high-frequency power supply 21A is larger than the magnitude of the high-frequency current which can be supplied from the high-frequency power supply 21B is shared by the control section 26A and 26B, an operation is performed for enabling the function, as the return electrode, of only the neutral electrode 3A which is connected to the power supply apparatus 1A while inhibiting the high-frequency current from being simultaneously applied from the treatment instruments 2A and 2B. Thus, according to such an operation, either the circuit CP1 or the circuit CP2 as described above is formed when the treatment of the intended living tissue of the subject is performed.

Further, for example, when information that the magnitude of the high-frequency current which can be supplied from the high-frequency power supply 21B is larger than the magnitude of the high-frequency current which can be supplied from the high-frequency power supply 21A is shared by the control section 26A and 26B, an operation is performed for enabling the function, as the return electrode, of only the neutral electrode 3B which is connected to the power supply apparatus 1B while inhibiting the high-frequency current from being simultaneously applied from the treatment instruments 2A and 2B. Thus, according to such an operation, either the circuit CP3 or the circuit CP4 as described above is formed when the treatment of the intended living tissue of the subject is performed.

Further, for example, when information that the magnitude of the high-frequency current which can be supplied from the high-frequency power supply 21A is equal to the magnitude of the high-frequency current which can be supplied from the high-frequency power supply 21B is shared by the control section 26A and 26B, an operation is performed for allowing the high-frequency current to be simultaneously applied from the treatment instruments 2A and 2B only when the neutral electrode 3A is connected to the power supply apparatus 1A and also the neutral electrode 3B is connected to the power supply apparatus 1B. Thus, according to such an operation, the circuit CP1 and the circuit CP3 as described above are simultaneously formed when the treatments of the intended living tissues of the subject are performed (see FIG. 7). FIG. 7 is a diagram for explaining an example, which is different from the examples of FIGS. 3-6, of the circuits which are formed when treatments of the living tissues are performed using the treatment system according to the embodiment.

On the other hand, according to the present embodiment, for example, when information that the neutral electrode 3A is presently connected to the power supply apparatus 1A and also the neutral electrode 3B is presently connected to the power supply apparatus 1B is shared by the control section 26A and 26B, the operation for allowing the high-frequency current to be simultaneously applied from the treatment instruments 2A and 2B may be performed, irrespective of the comparison result of the comparison between the magnitude of the high-frequency current which can be supplied from the high-frequency power supply 21A and the magnitude of the high-frequency current which can be supplied from the high-frequency power supply 21B. Thus, according to such an operation, the circuit CP1 and the circuit CP3 as described above are simultaneously formed when the treatments of the intended living tissues of the subject are performed (see FIG. 7).

Further, according to the present embodiment, for example, the operation for allowing the high-frequency current to be simultaneously applied from the treatment instruments 2A and 2B may be performed only when information that operations for allowing the high-frequency current to be simultaneously supplied are performed at both of the input operation sections 13A and 13B is shared by the control section 26A and 26B. Thus, according to such an operation, the circuit CP1 and the circuit CP3 as described above are simultaneously formed when the treatments of the intended living tissues of the subject are performed (see FIG. 7).

It is noted that the present invention is not limited to the foregoing embodiments and it is a matter of course that various modifications and applications are possible within a range not departing from the gist of the invention.

What is claimed is:

1. A treatment system for use with a living tissue, the treatment system comprising:
 a first power supply apparatus configured to be connectable with a first electric surgical device and a first neutral electrode, the first power supply apparatus including:
  a first high-frequency power supply configured to supply high-frequency current to the first electric surgical device bused on a first operation instruction signal,
  a first detector configured to detect whether the first neutral electrode is connected,
  a first processor programmed to control the first power supply apparatus,
  a first switch configured to switch a path of the high-frequency current collected by the first neutral electrode, and
  a third switch configured to switch a first path connecting the first high-frequency power supply section and the first electric surgical-device into a conducting state or a non-conducting state; and
 a second power supply apparatus configured to be connectable with a second electric surgical device and a second neutral electrode, in which the first power supply apparatus and the second power supply apparatus are electrically connected with each other through a connector section and the living tissue is treated while transmission and reception of information is performed between the first power supply apparatus and the second power supply apparatus, the second power supply apparatus including:
  a second high-frequency power supply configured to supply high-frequency current to the second electric surgical device based on a second operation instruction signal,
  a second detector configured to detect whether the second neutral electrode is connected,
  a second processor programmed to control the second power supply apparatus,
  a second switch configured to switch a path of the high-frequency current collected by the second neutral electrode, and
  a fourth switch configured to switch a second path connecting the second high-frequency power supply section and the second electric surgical device into a conducting state or a non-conducting state; wherein:
 in a case where the first processor and the second processor determine that the first detector detects the first neutral electrode and that the second detector does not detect the second neutral electrode, the first processor and the second processor are configured to:
  control the first switch and the second switch such that the high-frequency current collected by the first neutral electrode flows to the first high-frequency power supply when the first operation instruction signal is inputted to the first high-frequency power supply, and
  control the first switch and the second switch such that the high-frequency current collected by the first neutral electrode flows to the second high-frequency power supply section through the connector section when the second operation instruction signal is inputted to the second high-frequency power supply, and in a case where the first processor and the second processor determine that the second detector detects the second neutral electrode and that the first detector does not detect the first neutral electrode, the first processor and the second processor are configured to:

control the first switch section and the second switch section such that the high-frequency current collected by the second neutral electrode flows to the first high-frequency power supply through the connector section when the first operation instruction signal is inputted to the first high-frequency power supply, control the first switch and the second switch such that the big-frequency current collected by the second neutral electrode flows to the second high-frequency power supply when the second operation instruction signal is inputted to the second high-frequency power supply, control the third switch and the fourth switch such that the first path is in the conducting state and the second path is in the non-conducting state when the first operating instruction signal is inputted to the first high-frequency power supply, and control the third switch and the fourth switch such that the first path is in the non-conducting state and the second path is in the conducting state when the second operation instruction signal is inputted to the second high-frequency power supply.

2. The treatment system according to claim 1, wherein when one of the first detector and the second detector detects connection, the first processor or the second processor are configured to perform control to disable a function of the other detector.

3. The treatment system according to claim 1, wherein when, after one of the first detector and the second detector detects connection, another of the first detector and the second detector detects connection, the first processor and the second processor are configured to perform control to notify an error.

4. The treatment system according to claim 1, wherein information concerning magnitude of energy capable of being supplied from the first high-frequency power supply and the second high-frequency power supply is transmitted and received between the first power supply apparatus and the second power supply apparatus, and the first processor and the second processor are configured to perform control to disable a function of the second detector, when the first processor and the second processor determine that the magnitude of energy capable of being supplied from the first high-frequency power supply is larger than the magnitude of energy capable of being supplied from the second high-frequency power supply, and perform control to disable a function of the first detector, when the first processor and the second processor determine that the magnitude of energy capable of being supplied from the second high-frequency power supply is larger than the magnitude of energy capable of being supplied from the first high-frequency power supply.

5. A treatment system for use with a living tissue, the treatment system comprising:

a first power supply apparatus configured to be connectable with a first electric surgical device and a first neutral electrode, the first power supply apparatus including:
a first high-frequency power supply configured to supply high-frequency current to the first electric surgical device based on a first operation instruction signal,
a first detector configured to detect whether the first neutral electrode is connected,
a first processor programmed to control the first power supply apparatus; and a second power supply apparatus configured to be connectable with a second electric surgical device and a second neutral electrode, in which the first power supply apparatus and the second power supply apparatus are electrically connected with each other through a connector section and the living tissue is treated while transmission and reception of information is performed between the first power supply apparatus and the second power supply apparatus, the second power supply apparatus including:
a second high-frequency power supply configured to supply high-frequency current to the second electric surgical device based on a second operation instruction signal,
a second detector configured to detect whether the second neutral electrode is connected,
a second processor programmed to control the second power supply apparatus; wherein:

in a case where the first processor and the second processor determine that the first detector detects the first neutral electrode and that the second detector does not detect the second neutral electrode, the first processor and the second processor are configured to perform control to:
disable supply of the high-frequency current from the second high-frequency power supply to the second electric surgical device when the first operation instruction signal is inputted to the first high-frequency power supply,
disable supply of the high-frequency current from the first high-frequency power supply to the first electric surgical device when the second operation instruction signal is inputted to the second high-frequency power supply;

in a case where the first processor and the second processor determine that the second detector detects the second neutral electrode and that the first detector does not detect the first neutral electrode, the first processor and the second processor are configured to perform control to:
disable supply of the high-frequency current from the second high-frequency power supply to the second electric surgical device when the first operation instruction signal is inputted to the first high-frequency power supply, and
disable supply of the high-frequency current from the first high-frequency power supply to the first electric surgical device when the second operation instruction signal is inputted to the second high-frequency power supply; and when one of the first detector and the second detector detects connection, the first processor or the second processor are configured to perform control to disable a function of the other detector.

6. A treatment system for use with a living tissue, the treatment system comprising:
- a first power supply apparatus configured to be connectable with a first electric surgical device and a first neutral electrode, the first power supply apparatus including:
  - a first high-frequency power supply configured to supply high-frequency current to the first electric surgical device based on a first operation instruction signal,
  - a first detector configured to detect whether the first neutral electrode is connected, and
  - a first processor programmed to control the first power supply apparatus; and
- a second power supply apparatus configured to be connectable with a second electric surgical device and a second neutral electrode, in which the first power supply apparatus and the second power supply apparatus are electrically connected with each other through a connector section and the living tissue is treated while transmission and reception of information is performed between the first power supply apparatus and the second power supply apparatus, the second power supply apparatus including:
  - a second high-frequency power supply configured to supply high-frequency current to the second electric surgical device based on a second operation instruction signal,
  - a second detector configured to detect whether the second neutral electrode is connected, and
  - a second processor programmed to control the second power supply apparatus; wherein:
- information concerning magnitude of energy capable of being supplied from the first high-frequency power supply and the second high-frequency power supply is transmitted and received between the first power supply apparatus and the second power supply apparatus, and
- in a case where the first processor and the second processor determine that the first detector detects the first neutral electrode and that the second detector does not detect the second neutral electrode, the first processor and the second processor are configured to perform control to:
  - disable supply of the high-frequency current from the second high-frequency power supply to the second electric surgical device when the first operation instruction signal is inputted to the first high-frequency power supply, and
  - disable supply of the high-frequency current from the first high-frequency power supply to the first electric surgical device when the second operation instruction signal is inputted to the second high-frequency power supply;
- in a case where the first processor and the second processor determine that the second detector detects the second neutral electrode and that the first detector does not detect the first neutral electrode, the first processor and the second processor are configured to perform control to:
  - disable supply of the high-frequency current from the second high-frequency power supply to the second electric surgical device when the first operation instruction signal is inputted to the first high-frequency power supply, and
  - disable supply of the high-frequency current from the first high-frequency power supply to the first electric surgical device when the second operation instruction signal is inputted to the second high-frequency power supply; and
- the first processor and the second processor are configured to perform control to:
  - disable a function of the second detector, when the first processor and the second processor determine that the magnitude of energy capable of being supplied from the first high-frequency power supply is larger than the magnitude of energy capable of being supplied from the second high-frequency power supply, and
  - disable a function of the first detector, when the first processor and the second processor determine that the magnitude of energy capable of being supplied from the second high-frequency power supply is larger than the magnitude of energy capable of being supplied from the first high-frequency power supply.

* * * * *